(12) United States Patent
Kitazawa et al.

(10) Patent No.: US 7,883,901 B2
(45) Date of Patent: Feb. 8, 2011

(54) BIOGENIC SUBSTANCE DETECTOR AND BIOGENIC SUBSTANCE DETECTION METHOD

(75) Inventors: Rie Kitazawa, Shiojiri (JP); Fumio Takagi, Chino (JP)

(73) Assignee: Seiko Epson Corporation (JP)

( * ) Notice: Subject to any disclaimer, the term of this patent is extended or adjusted under 35 U.S.C. 154(b) by 199 days.

(21) Appl. No.: 12/247,500

(22) Filed: Oct. 8, 2008

(65) Prior Publication Data

US 2009/0111192 A1    Apr. 30, 2009

(30) Foreign Application Priority Data

Oct. 26, 2007    (JP)    ............... 2007-279095

(51) Int. Cl.
  *G01N 21/76*    (2006.01)
  *G01N 21/05*    (2006.01)

(52) U.S. Cl. ............... 436/172; 422/52; 422/57; 422/58; 422/100; 422/102; 436/165

(58) Field of Classification Search ............ 422/56–58, 422/100, 102, 52; 436/172, 165
See application file for complete search history.

(56) References Cited

U.S. PATENT DOCUMENTS

| | | | | |
|---|---|---|---|---|
| 3,799,742 A | * | 3/1974 | Coleman | 422/61 |
| 4,118,280 A | * | 10/1978 | Charles et al. | 435/287.3 |
| 4,330,627 A | * | 5/1982 | Thomas et al. | 435/288.5 |
| 4,585,623 A | * | 4/1986 | Chandler | 422/57 |
| 4,673,657 A | * | 6/1987 | Christian | 436/501 |
| 4,791,060 A | * | 12/1988 | Chandler | 435/287.2 |
| 4,806,316 A | * | 2/1989 | Johnson et al. | 422/100 |
| 5,147,607 A | * | 9/1992 | Mochida | 422/57 |
| 5,225,163 A | * | 7/1993 | Andrews | 422/61 |
| 5,286,454 A | * | 2/1994 | Nilsson et al. | 422/102 |
| 5,472,671 A | * | 12/1995 | Nilsson et al. | 422/102 |
| 5,677,133 A | * | 10/1997 | Oberhardt | 435/7.1 |
| 5,681,529 A | * | 10/1997 | Taguchi et al. | 422/61 |
| 5,700,695 A | * | 12/1997 | Yassinzadeh et al. | 436/180 |
| 5,731,212 A | * | 3/1998 | Gavin et al. | 436/526 |
| 5,922,593 A | * | 7/1999 | Livingston | 435/288.5 |
| 6,176,991 B1 | * | 1/2001 | Nordman | 204/601 |
| 6,238,911 B1 | * | 5/2001 | Kasahara | 435/288.4 |
| 6,309,890 B1 | * | 10/2001 | Tegeler et al. | 436/180 |

(Continued)

FOREIGN PATENT DOCUMENTS

JP    3557419    5/2004

(Continued)

*Primary Examiner*—Arlen Soderquist
(74) *Attorney, Agent, or Firm*—Harness, Dickey & Pierce, P.L.C.

(57) ABSTRACT

A biogenic substance detector with high reaction efficiency and detection sensitivity is obtained.

The biogenic substance detector includes: a plurality of chambers 1011 for hybridizing a target and a probe; and a passage 1012 provided between the chambers 1011. The cross-sectional area of the passage 1012 taken perpendicularly to the chamber-passage alignment direction is smaller than the cross-sectional area of each chamber 1011 taken perpendicularly to the chamber-passage alignment direction, and a probe-fixing area 1013 is provided over the entire inside wall of each chamber 1011. One kind of probe is fixed in one chamber 1011. In the hybridization step, the sample solution is made to move back and forth within the chambers 1011 and the passage 1012 using a pump 102.

3 Claims, 5 Drawing Sheets

U.S. PATENT DOCUMENTS

| | | | |
|---|---|---|---|
| 6,742,661 B1 * | 6/2004 | Schulte et al. | 210/511 |
| 6,811,752 B2 * | 11/2004 | Barbera-Guillem | 422/100 |
| 6,852,284 B1 * | 2/2005 | Holl et al. | 422/68.1 |
| 7,011,793 B2 * | 3/2006 | Zhou et al. | 422/100 |
| 2005/0255007 A1 | 11/2005 | Yamada et al. | |
| 2007/0099290 A1 | 5/2007 | Iida et al. | |

FOREIGN PATENT DOCUMENTS

| | | |
|---|---|---|
| JP | 2005-091135 | 4/2005 |
| JP | 2005-323519 | 11/2005 |
| JP | 3746756 | 12/2005 |
| JP | 2006-170654 | 6/2006 |
| JP | 2006-234590 | 9/2006 |
| JP | 2006-284323 | 10/2006 |
| JP | 2007-040969 | 2/2007 |
| WO | WO 2005-24436 | 3/2005 |

* cited by examiner

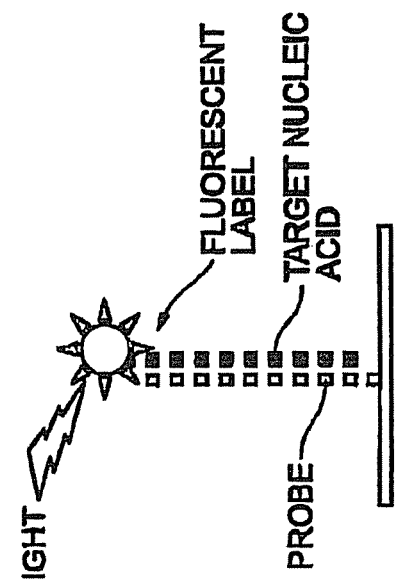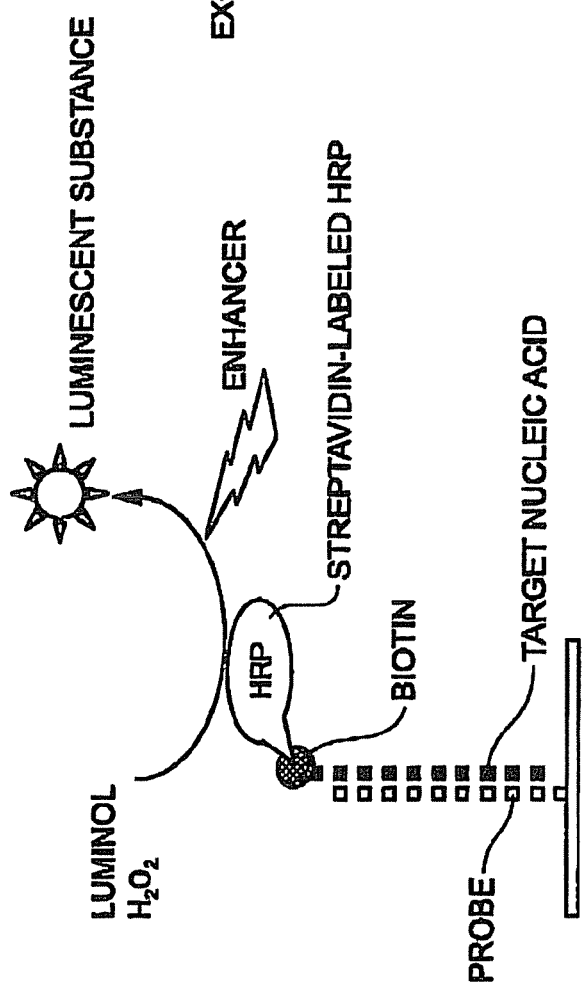

BIOGENIC SUBSTANCE DETECTOR AND BIOGENIC SUBSTANCE DETECTION METHOD

CROSS-REFERENCES TO RELATED APPLICATIONS

This application relates to and claims priority from Japanese Patent Application No. 2007-279095, filed on Oct. 26, 2007, the entire disclosure of which is incorporated herein by reference.

BACKGROUND

1. Field of the Invention

The invention relates to a biogenic substance detector and biogenic substance detection method for detecting a biogenic substance, such as nucleic acid molecules having a specific base sequence.

2. Description of Related Art

A DNA microarray is one technique of testing whether or not a specific gene from which a certain disease derives exists in specimen material such as blood or tissue cells. The DNA microarray tests whether a target gene exists or not by causing a reaction (hybridization) between a probe gene fixed to a base plate and a gene in a specimen material. Conventionally, means of enhancing reaction efficiency between a specific gene in a specimen material and a probe gene has been devised to improve the accuracy of detecting that specific gene contained in the specimen material.

For example, Japanese Patent No. 3746756 discloses a method for enhancing reaction efficiency by filling a space between a base plate, onto which a probe is fixed, and a plate member and causing a relative motion between the base plate and the plate member, thereby agitating the sample solution. Also, Japanese Patent No. 3557419 discloses a method for enhancing reaction efficiency by distributing fine particles in a sample solution and agitating the sample solution.

In the methods disclosed in Japanese Patents Nos. 3746756 and 3557419, the sample solution is agitated by, for example, rotating a DNA microarray. Meanwhile, as an example of a method for enhancing reaction efficiency without using a mechanism for moving a microarray, Japanese Patent Application Laid-open (Kokai) Publication No. 2007-40969 discloses a biochemical reaction cassette including a fluid resistance unit for reducing the cross-sectional area of a passage in order to control the flow of a fluid in chambers for having a nucleic-acid-detecting probe react with a specimen.

If plural kinds of probes are used for detection with the biochemical reaction cassette disclosed in Japanese Patent Application Laid-open (Kokai) Publication No. 2007-40969, the plural probes are placed in one chamber. As main methods for detecting a substance that has reacted with probes, there are: a method using a fluorescent labeling reagent and a method using a chemiluminescent substance. If the method using the fluorescent labeling reagent is utilized, the fluorescent labeling reagent will be bonded to a substance to be detected. Meanwhile, if the method using the chemiluminescent substance is utilized, an enzyme bonded to a substance to be detected serves as a catalyst to generate a luminescent substance. As a result of using the method using the chemiluminescent substance, the generated luminescent substance will diffuse in one chamber and it is hard to tell which probe from among the plural probes in one chamber has detected the luminescent substance. On the other hand, the method using the fluorescent labeling reagent does not have such a problem of diffusion of the labeling agent. Therefore, the method disclosed in Japanese Patent Application Laid-Open (Kokai) Publication No. 2007-40969 is utilized on the condition that the fluorescent labeling reagent is used for detection after hybridization. However, since the method using the chemiluminescent substance can achieve highly-sensitive detection at a lower cost than the method using the fluorescent labeling reagent, it is preferable to utilize the method using the chemiluminescent substance as a detection method.

SUMMARY

It is an object of the present invention to provide a biogenic substance detector with high reaction efficiency and detection sensitivity.

A biogenic substance detector according to an aspect of the invention includes: a plurality of chambers, each of which has an area for fixing a probe for detecting a specific biogenic substance contained in a sample solution and is used to have the biogenic substance and the probe react with each other; a passage provided between the chambers; and a pump for allowing the sample solution to move back and forth within the chambers and the passage along a chamber-passage alignment direction; wherein the passage having a cross-sectional area taken perpendicularly to the chamber-passage alignment direction is smaller than a cross-sectional area of each chamber taken perpendicularly to the chamber-passage alignment direction.

As the invention has chambers connected by the passage, a plurality of kinds of targets can be detected at once by fixing different kinds of probes to the chambers, with only one kind of probe for each chamber. If only one kind of probe is used in one chamber, even if a chemiluminescent substance that is a solution with a luminescent substance floating therein is used for detection of the reaction result, there will be no problem of diffusion of the luminescent substance in the chamber and inability to tell which probe from among the plurality of probes in one chamber has reacted with the target.

Moreover, according to the invention, the cross-sectional area of the passage taken perpendicularly to the chamber-passage alignment direction is smaller than the parallel cross-sectional area of each chamber. Consequently, there is an advantageous effect of agitating the sample solution in the chamber by changing the flow of the liquid when the sample solution flows from a passage with a small cross-sectional area to a chamber with a larger cross-section area. As a result of agitation of the sample solution in the chamber, a larger amount of a target biogenic substance will come into contact with the probe in a short period of time, thereby enhancing reaction efficiency.

Furthermore, a pump is used to move the sample solution back and forth within the chambers and the passage, so a larger amount of a target biogenic substance will come into contact with the probe, thereby enhancing reaction efficiency.

It is also favorable to have the area for fixing the probe provided over the entire inside wall surface of each chamber. As a result, the entire inside wall surface of the chamber can come into contact with the probe and the target biogenic substance, thereby enhancing reaction efficiency.

Moreover, it is favorable to have the chambers and the passage made in a transparent plate. As a result, the inside of the chambers can be observed from outside the chambers. Therefore, reaction processing and detection processing can be performed by the same device, the size of the device can be reduced, and the efficiency of the processing can be enhanced.

Each chamber may have a lenticular area on its outside wall. As a result, light emitted from inside of the chamber will converge, and detection sensitivity for detecting the reaction result can be further enhanced.

A biogenic substance detection method according to another aspect of the invention includes: a reaction step of supplying a sample solution to a plurality of chambers connected via a passage and having a specific biogenic substance contained in the sample solution react with a probe fixed in the chambers to detect the biogenic substance; and a detection step of detecting the biogenic substance that has reacted with the probe; wherein in the reaction step, the sample solution is made to move back and forth within the chambers and the passage along a chamber-passage alignment direction, and the passage having a cross-sectional area taken perpendicularly to the chamber-passage alignment direction is smaller than a cross-sectional area of each chamber taken perpendicularly to the chamber-passage alignment direction.

The cross-sectional area of the passage taken perpendicularly to the chamber-passage alignment direction is smaller than the parallel cross-sectional area of each chamber according to the invention. Consequently, there is an advantageous effect of agitating the sample solution in the chamber by changing the flow of the liquid when the sample solution flows from a passage with a small cross-sectional area to a chamber with a larger cross-section area. As a result of agitation of the sample solution in the chamber, a larger amount of a target biogenic substance will come into contact with the probe in a short period of time, thereby enhancing reaction efficiency.

Furthermore, a pump is used to move the sample solution back and forth within the chambers and the passage, so a larger amount of a target biogenic substance will come into contact with the probe, thereby enhancing reaction efficiency.

It is also favorable to have one kind of probe fixed in each of the chambers. According to the invention, plural kinds of targets can be detected at once by fixing different kinds of probes to the chambers, with only one kind of probe for each chamber. If only one kind of probe is used in one chamber, even if a chemiluminescent substance that is a solution with a luminescent substance floating therein is used for detection of the reaction result, there will be no problem of diffusion of the luminescent substance in one chamber and inability to tell which probe from among the plurality of probes in one chamber has reacted with the target.

Moreover, it is favorable to have the probe fixed to the entire inside wall surface of each chamber. As a result, the entire inside wall surface of the chamber can come into contact with the probe and the target biogenic substance, thereby enhancing reaction efficiency.

Furthermore, in the detection step, it is favorable to detect the biogenic substance that has reacted with the probe, by a method using a chemiluminescent substance. Since generally the amount of produced luminescent substance can be increased by increasing the amount of a substrate to be added, it is easy to enhance detection sensitivity.

It is also favorable to have the chambers and the passage made in a transparent plate; and in the detection step, it is favorable to measure luminescence through the chambers. As a result, reaction processing and detection processing can be performed by the same device, the size of the device can be reduced and the efficiency of the processing can be enhanced.

Other aspects and advantages of the invention will be apparent from the following description and the appended claims.

BRIEF DESCRIPTION OF THE DRAWINGS

FIG. 4A is a diagram explaining the principle of a detection method using a chemiluminescent substance, and FIG. 4B is a diagram explaining the principle of a detection method using a fluorescent labeling reagent.

DETAILED DESCRIPTION OF PREFERRED EMBODIMENTS

An embodiment of the present invention will be explained below with reference to the attached drawings.

Figure 1:
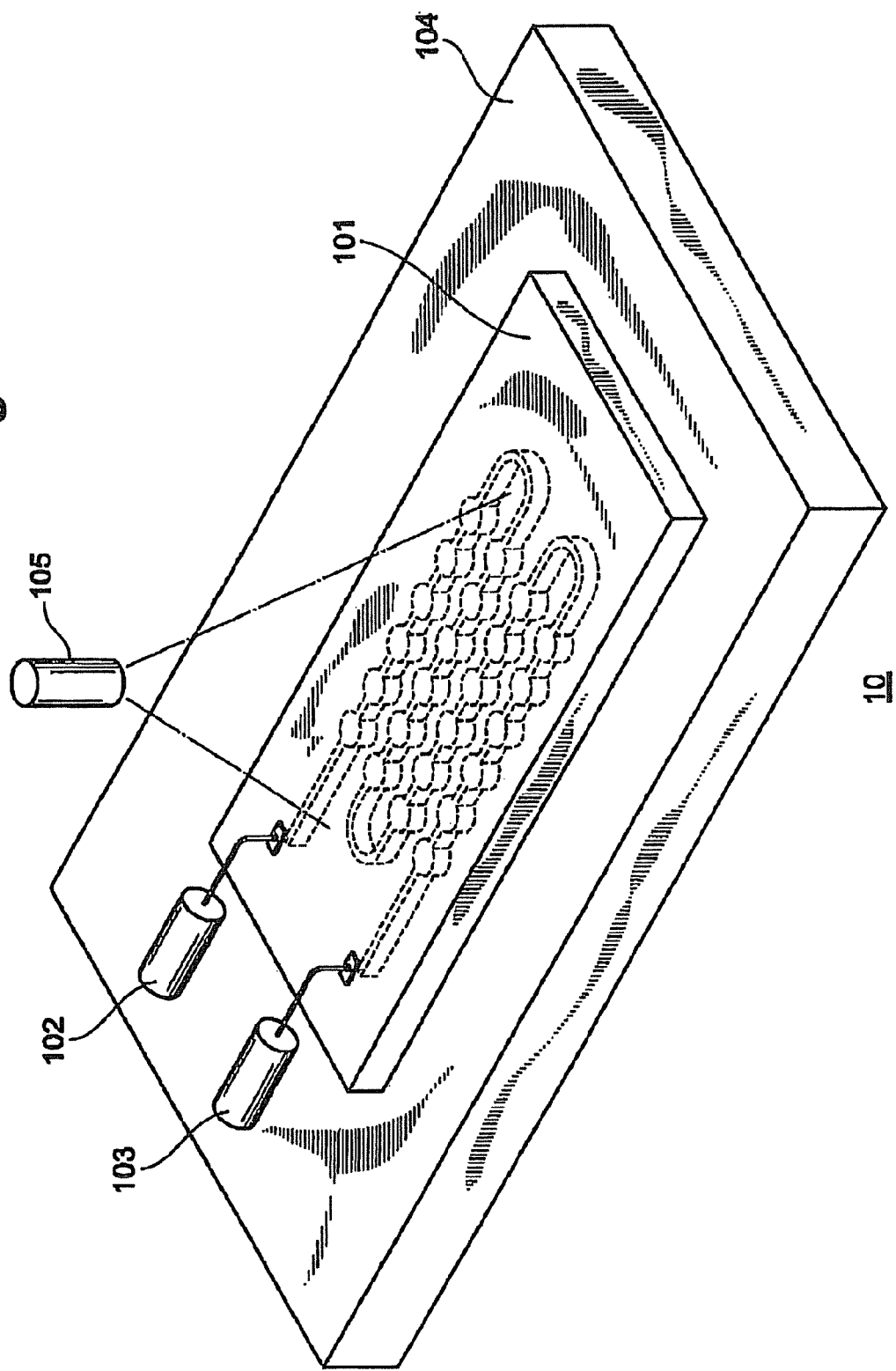
FIG. 1 is a perspective view showing the configuration of a nucleic acid detector according to an embodiment of the invention.

FIG. 1 is a perspective view showing the configuration of a nucleic acid detector (biogenic substance detector) 10 according to an embodiment of the invention. As shown in FIG. 1, the nucleic acid detector 10 includes a detection cartridge 101, a pump 102, a sample container 103, a stage 104, and a CCD camera 105.

Figure 2:
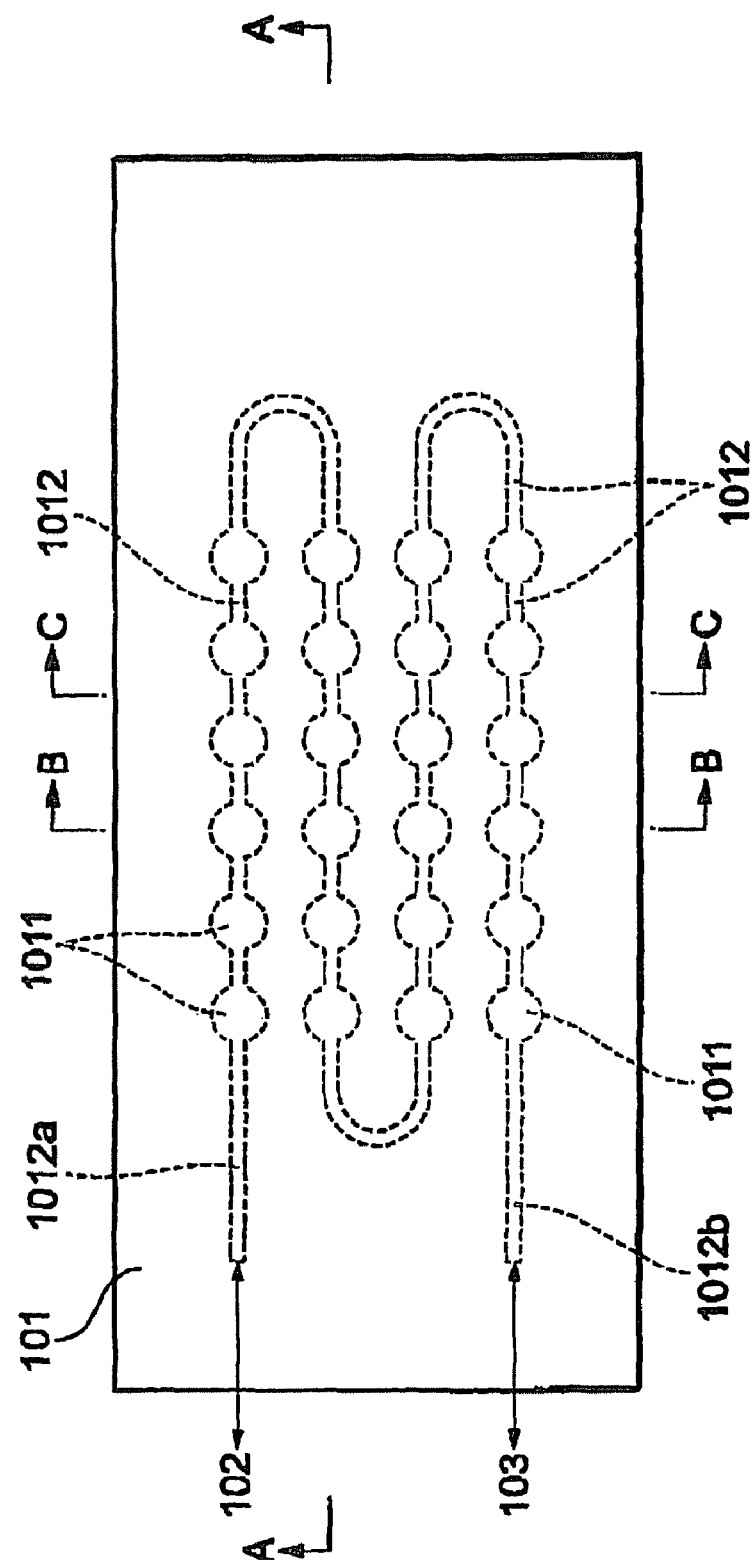
FIG. 2 is a top view of a detection cartridge according to the first embodiment of the invention.
Figure 3A:
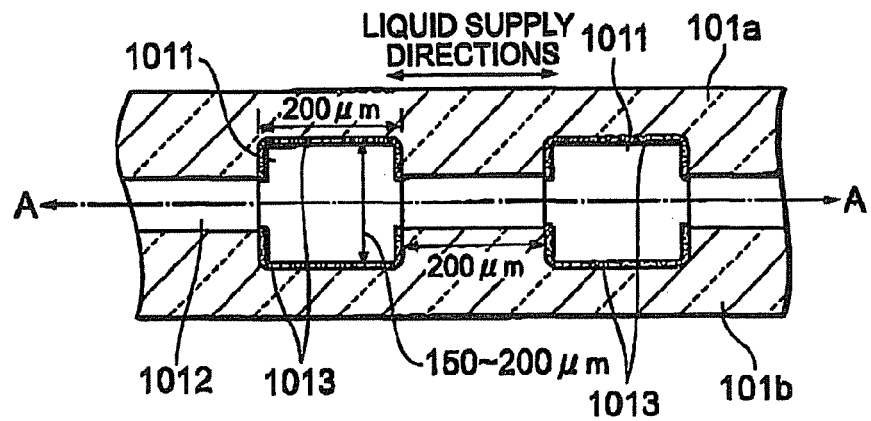
FIG. 3A is a fragmentary cross-sectional view of the detection cartridge as taken along line A-A in FIG. 2.
Figure 3B:
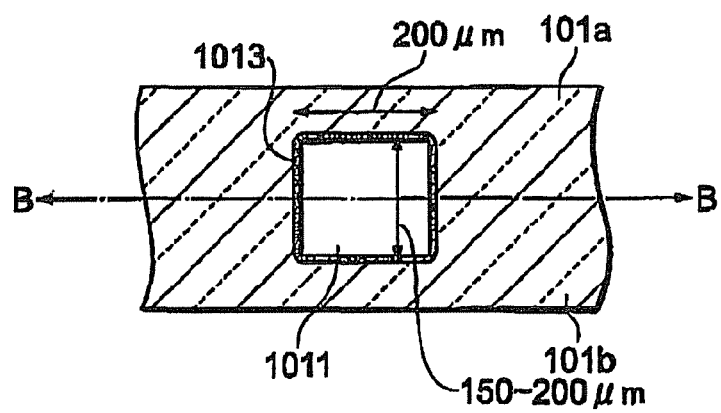
FIG. 3B is a fragmentary cross-sectional view of the detection cartridge as taken along line B-B in FIG. 2.
Figure 3C:
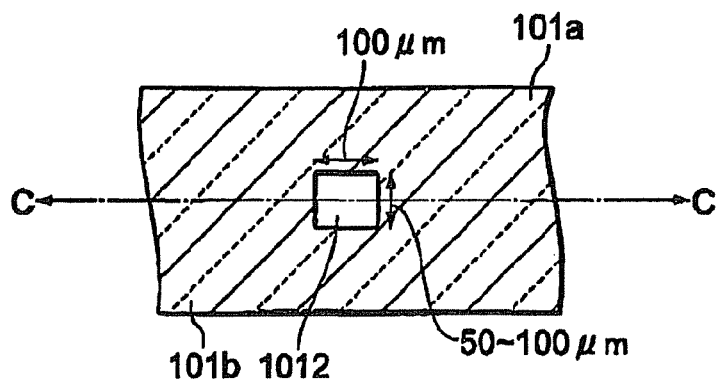
FIG. 3C is a fragmentary sectional view of the detection cartridge as taken along line C-C in FIG. 2.

FIG. 2 is a top view of the detection cartridge 101. FIG. 3A is a fragmentary cross-sectional view of the detection cartridge 101 as taken along line A-A in FIG. 2, FIG. 3B is a fragmentary cross-sectional view of the detection cartridge 101 as taken along line B-B in FIG. 2, and FIG. 3C is a fragmentary sectional view of the detection cartridge 101 as taken along line C-C in FIG. 2. As shown in these drawings, the detection cartridge 101 includes a plurality of chambers 1011 and a passage 1012 connecting these chambers 1011. One end portion of the passage 1012a is connected to the pump 102, while the other end portion of the passage 1012b is connected to the sample container 103.

As shown in FIGS. 3A to 3C, the detection cartridge 101 is constructed by pasting two transparent base plates 101a, 101b together. Each transparent base plate 101a, 101b has a recess that forms part of the chambers 1011 and the passage 1012. The three-dimensional chambers 1011 and passage 1012 are formed by pasting the transparent base plates 101a, 101b together. The transparent base plates 101a, 101b can be made of, for example, glass.

Regarding the size of each chamber 1011 and the passage 1012 as shown in FIGS. 3A to 3C, the chamber 1011 can be 200 μm long in a sample-solution-flow direction and 150 to 200 μm deep, and the passage 1012 can be 200 μm long in the sample-solution-flow direction, 100 μm wide, and 50 to 100 μm deep. The cross-sectional area (cross-section shown in FIG. 3C) of the passage 1012 taken perpendicular to the chamber-passage alignment direction is smaller than the parallel cross-sectional area (cross-section shown in FIG. 3B) of the chamber 1011 taken perpendicular to the chamber-passage alignment direction.

The shape of the chamber 1011 is not limited to the circular shape shown in FIG. 2, and any shape, such as an ellipse or a quadrangle with rounded corners, can be utilized as long as that shape does not easily allow accumulation of gas bubbles in the chamber 1011. Also, the cross-sectional shape of the passage 1012 as taken perpendicularly to the sample-solution-flow direction is not limited to the shape shown in FIG. 3C, and any shape, such as a circular shape, can be utilized as long as that shape does not easily allow accumulation of gas bubbles in the passage 1012.

Each chamber 1011 has a probe-fixing area 1013 on its inside wall. The probe-fixing area 1013 is an area for applying a probe and is provided over the entire inside wall surface of the chamber 1011. As a result, the probe and the target can come into contact with each other over the entire inside wall surface of the chamber 1011, thereby enhancing reaction efficiency.

A substance capable of trapping a target substance ("target") contained in a specimen sample such as blood, urine, saliva, or spinal fluid can be used as the probe. If the target is nucleic acids such as DNA or RNA, nucleic acids that can hybridize (complementarily bind) with the target nucleic acids, or a nucleotide (oligonucleotide) or the like can be used as the probe. Examples of such nucleic acids include cDNA and PCR products.

Incidentally, the target is not limited to nucleic acids, and may be, for example, specific proteins. In this case, a substance capable of trapping these proteins in a specific manner (for example, by means of adsorption or binding) can be used as the probe. Specific examples of the probe include proteins such as antigens, antibodies, receptors, and enzymes, or peptide (oligopeptide).

The probe can be applied to the probe-fixing area 1013, using, for example, a non-contact or contact spotter. In this embodiment, different kinds of probes are fixed to the chambers 1011, with only one kind of probe for each chamber 1011. As a result, it is possible to detect plural kinds of targets at once.

Incidentally, the probe-fixing area 1013 may undergo surface treatment as necessary. An example of the surface treatment includes processing for ensuring fixation of the probe to the surface of the probe-fixing area 1013 (solid-phase processing).

Examples of the solid-phase processing include processing for introducing a functional group that forms a covalent bond or an ionic bond with the probe, such as a thiol group, amino group, isocyanate group, chloride group, or epoxy group. If the transparent base plates 101a, 101b are glass base plates, the above-mentioned functional groups can be introduced by treating the probe with coupling agents having the above-mentioned functional groups (such as silane coupling agents, zirconium coupling agents, or aluminum coupling agents).

If the probe is nucleic acids or a nucleotide, other examples of the solid-phase processing may include coat of poly-L-lysine and formation of a plasma polymerization film. Also, a surface treatment of coating activated ester on the base plates may be performed and, at the same time, the ends of the probe (end of sense strand contained in double-stranded DNA fragment) may be aminated. As a result, the probe is firmly fixed to the probe-fixing area 1013 via the covalent bond between the activated ester and the amino group.

On the other hand, if the probe is a protein or peptide, processing such as a surface treatment of introducing an active group for forming an amide bond with proteins to the surface of the probe-fixing area 1013 is performed. As a result, the probe can be firmly fixed to the probe-fixing area 1013. Examples of the active group include a carbonyl imidazole group or an epoxy group.

The pump 102 may be, for example, a syringe pump or a micro-pump. The pump 102 is connected to one end of the passage 1012a via a capillary tube made of, for example, fluororesin, polyether ether ketone (PEEK) resin, or silicon resin, so that the sample solution can be supplied back and forth through all the chambers 1011 and the passage 1012.

The sample container 103 is a container for storing a sample solution. The sample container 103 is connected to the other end of the passage 1012b, opposite the end of the passage 1012a connected to the pump 102, via a capillary tube made of, for example, fluororesin, polyether ether ketone (PEEK) resin, or silicon resin, so that the sample solution is supplied from this sample container 103 via the passage 1012b into the chambers 1011. When the pump 102 is used to supply the sample solution back and forth, the sample solution that spills out of the passage 1012b flows into the sample container 103 and then returns to the passage 1012b.

The stage 104 is a stage to which the detection cartridge 101 is fixed. The CCD camera 105 is used to measure the luminescence intensity of a chemiluminescent substance produced during the processing for detecting a hybridization reaction. The CCD camera 105 is set at a position where it can detect light emitted from the detection cartridge 101.

Next, processing for hybridizing the target (nucleic acid) with the probe (reaction step) and processing for detecting the hybridization (detection step), using the nucleic acid detector 10 according to this embodiment will be explained below.

First, the inside space of the detection cartridge 101 in which the probe is fixed to the probe-fixing area 1013 (the space formed with the chambers 1011 and the passage 1012) is filled with a blocking buffer, using the pump 102. The blocking buffer which has filled the inside space of the detection cartridge 101 is then moved back and forth within the detection cartridge 101, thereby blocking areas to which the probe is not fixed. Blocking is performed for about 10 minutes.

After the blocking buffer is ejected out of the detection cartridge 101 using the pump 102, the pump 102 is used to fill the detection cartridge 101 with a cleaning fluid and move the cleaning fluid, which has filled the detection cartridge 101, back and forth within the detection cartridge 101, thereby fully cleaning the inside space of the chambers 1011 and the passage 1012.

Subsequently, the detection cartridge 101 is filled with a biotin-labeled sample solution. Specifically speaking, the pump 102 is activated to supply the sample solution, which is contained in the sample container 103, through the passage 1012b into the detection cartridge 101.

A method for adjusting the biotin-labeled sample solution will be explained below. The sample solution includes a biogenic sample such as blood, urine, saliva, or spine fluid. The sample solution may be treated in advance, as necessary, to amplify the target nucleic acid by a PCR method. Specifically speaking, first and second primers are first added to the sample and cycle that has three temperature steps is performed. The first primer specifically binds with part of the target nucleic acid, and the second primer specifically binds with part of a nucleic acid that is complementary to the target nucleic acid. If the double-stranded nucleic acid containing the target nucleic acid binds with the first and second primers, the double-stranded nucleic acid containing the target nucleic acid is amplified because of an elongation reaction. After the double-stranded nucleic acid containing the target nucleic acid has been amplified sufficiently, a third primer is added to the sample and the temperature cycling is performed. The third primer can incorporate the biotin during the elongation reaction and specifically binds with part of the nucleic acid that is complementary to the target nucleic acid. If the nucleic acid which is complementary to the target nucleic acid binds with the third primer, the biotin-labeled target nucleic acid is amplified because of an elongation reaction. As a result, if the target nucleic acid is contained in the sample, the labeled target nucleic acid will be produced; or if the target nucleic acid is not contained in the sample, the labeled target nucleic acid will not be produced. Incidentally, the labeling substance is biotin in this embodiment, but other substances such as enzymes or luminescent substances may be used as the labeling substance.

Next, the biotin-labeled sample solution, which has filled the detection cartridge 101, is moved back and forth within the detection cartridge 101 and made to react (hybridize) with the probe fixed in the probe-fixing area 1013. It is favorable to have the hybridization performed for one to three hours.

The cross-sectional area of the passage 1012 taken perpendicularly to the chamber-passage alignment direction is smaller than the cross-sectional area of each chamber 1011 taken perpendicularly to the chamber-passage alignment direction according to this embodiment. As the sample solution flows from the passage 1012 with the small cross-sectional area into the chamber 1011 with the larger cross-sectional area, the flow of the sample solution changes, thereby bringing about an advantageous effect of agitating the sample solution in the chamber 1011. As a result of agitating the sample solution in the chamber 1011, a larger amount of target nucleic acid will come into contact with the probe in the probe-fixing area 1013 in a short period of time, thereby enhancing hybridization efficiency.

Next, after the biotin-labeled sample solution is ejected using the pump 102, the pump 102 is used to fill the inside of the detection cartridge 101 with a cleaning fluid and supplies the cleaning fluid, which has filled the detection cartridge 101, back and forth within the detection cartridge 101, thereby fully cleaning the inside of the chambers 1011 and the passage 1012.

Subsequently, the pump 102 is used to fill the detection cartridge 101 with a streptavidin-labeled chemiluminescent enzyme (HRP) liquid and move the HRP liquid back and forth within the detection cartridge 101 for about five minutes. After the HRP liquid is ejected, the detection cartridge 101 is filled with the cleaning fluid, which is then moved back and forth within the detection cartridge 101, thereby fully cleaning the inside of the chambers 1011 and the passage 1012.

Next, the pump 102 is used to fill the detection cartridge 101 with a solution containing a chemiluminescent substrate (luminol) and hydrogen peroxide. After the detection cartridge 101 is filled with the solution, the detection cartridge 101 is left still, without moving the solution back and forth within the detection cartridge 101, for about 10 to 30 seconds to wait for production of a chemiluminescent substance.

After the chemiluminescent substance is produced, luminescence intensity is measured with the CCD camera 105 to check whether a hybridization reaction has taken place or not.

FIG. 4A is a diagram explaining the principle of a detection method using a chemiluminescent substance. If the detection method using the chemiluminescent substance is utilized as shown in FIG. 4A, when biotin bonded with a target nucleic acid binds with a streptavidin-horseradish peroxidase (HRP) and a chemiluminescent substrate liquid (luminol and hydrogen peroxide) is then added thereto, the HRP reacts with the luminol and the hydrogen peroxide to produce a luminescent substance, thereby emitting light. Since the amount of produced luminescent substance can be increased by increasing the luminol and hydrogen peroxide, it is easy to enhance detection sensitivity.

FIG. 4B is a diagram explaining the principle of a detection method using a fluorescent labeling reagent. If the method using the fluorescent labeling reagent is utilized, when the fluorescent labeling reagent bonded with the target nucleic acid is irradiated with excitation light, the fluorescent labeling reagent produces luminescence. Since the luminescence intensity depends on the amount of fluorescent labeling reagent bonded with the target nucleic acid, it is more difficult to enhance detection sensitivity with this method than in the detection method using the chemiluminescent substance.

Therefore, it is better to utilize the method using the chemiluminescent substance in order to enhance detection sensitivity. If the method using the fluorescent labeling reagent is utilized, the fluorescent labeling reagent, which is an illuminant, is bonded with the target nucleic acid and, therefore, the position of the illuminant does not move. Consequently, even in the case of hybridization that uses a plurality of probes in one chamber, it is easy to tell which probe from among the plurality of probes has reacted. On the other hand, if the method using the chemiluminescent substance is utilized, the generated luminescent substance will be diffused in one chamber. Therefore, if a plurality of probes are used in one chamber, it is difficult to tell which probe from among the plurality of probes has detected the target biogenic substance. However, with the nucleic acid detector 10 according to the present invention, different kinds of probes are fixed to the chambers 1011, with only one kind of probe for each chamber 1011. As a result, even if the method using the chemiluminescent substance is utilized, there will be no problem of diffusion of the luminescent substance in the chamber and inability to tell which probe from among the plurality of probes has reacted, and it is possible to detect plural kinds of targets at once. Incidentally, the enzymes, substrates, and the like used for the detection with the chemiluminescent substance are not limited to those described above.

According to the embodiment described above, plural kinds of targets can be detected at once by fixing different kinds of probes to the chambers 1011 connected by the passage 1012, with only one kind of probe for each chamber 1011. Also, if only one kind of probe is used in each chamber, even if the hybridization result is detected by the method using the chemiluminescent substance, there will be no problem of diffusion of the luminescent substance in one chamber and inability to tell which probe from among the plurality of probes has reacted.

Moreover, since the cross-sectional area of the passage 1012 taken perpendicularly to the chamber-passage alignment direction is smaller than the parallel cross-sectional area of the chamber 1011 according to this embodiment, there is an advantageous effect of changing the flow of the sample solution at the boundary between the passage 1012 and the chambers 1011 and thereby agitating the sample solution in the chambers 1011. As the sample solution is agitated in each chamber 1011, the probe will come into contact with a larger amount of targets in a short period of time, thereby enhancing reaction efficiency.

Also, the pump 102 is used to move the sample solution back and forth in the chambers 1011 and the passage 1012 according to this embodiment. As a result, a larger amount of targets will come into contact with the probe, thereby enhancing reaction efficiency.

Moreover, the probe-fixing area 1013 is provided over the entire inside wall surface of the chamber 1011 according to this embodiment. As a result, the target can come into contact with the probe over the entire inside wall surface of the chamber 1011, thereby enhancing reaction efficiency.

Furthermore, the chambers 1011 and the passage 1012 are composed of the transparent base plates 101a, 101b. As a result, the inside of the chambers 1011 can be observed from outside the chambers 1011. Therefore, the reaction step and the detection step can be performed by the same device, the size of the device can be reduced, and the efficiency of the processing can be enhanced.

(Variation 1)

Figure 5A:
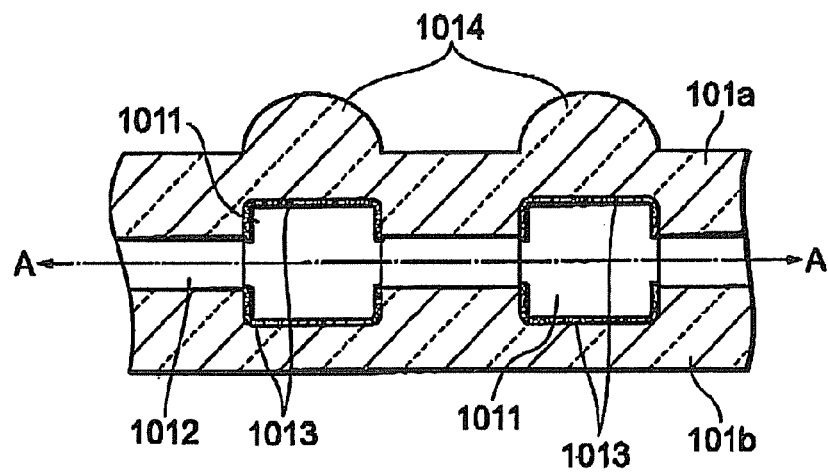
FIG. 5A and FIG. 5B are cross-sectional views of a detection cartridge according to Variation 1 of the invention.
Figure 5B:
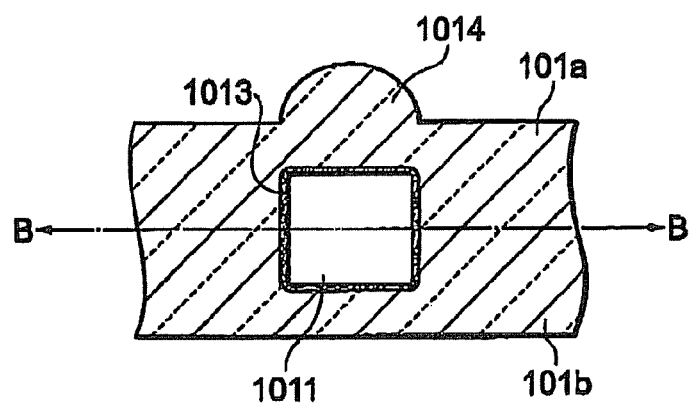

FIG. 5A and FIG. 5B show cross-sectional views illustrating the configuration of a detection cartridge 101 for a nucleic acid detector 10 according to variation 1 of the invention. FIG. 5A is a fragmentary cross-sectional view of the detection cartridge 101 as taken along line A-A in FIG. 2, and FIG. 5B is a fragmentary cross-sectional view of the detection cartridge 101 as taken along line B-B in FIG. 2. In variation 1, as shown in these cross-sectional views, lenticular portions 1014 are provided in areas corresponding to the outside wall of the chambers 1011 on the upper transparent base plate 101a. As a result, the light emitted from the luminescent substance is made to converge by the lenticular portions 1014 and, therefore, detection sensitivity can be further enhanced when the CCD camera 105 detects the luminescence.

(Variation 2)

Figure 6:
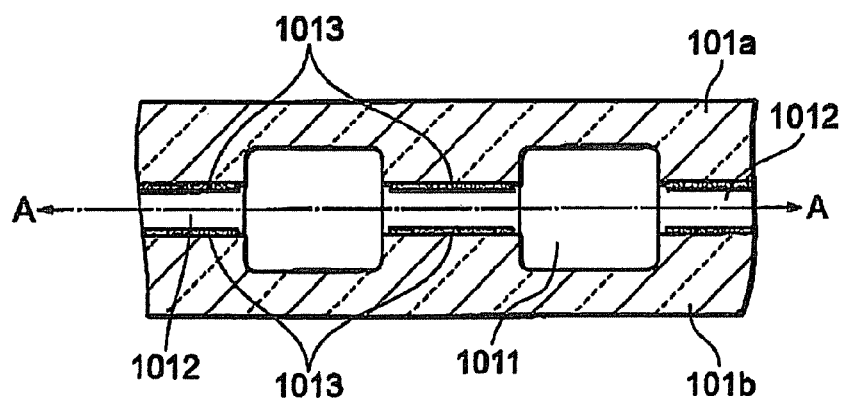
FIG. 6 is a cross-sectional view of a detection cartridge according to Variation 2 of the invention.

FIG. 6 is a cross-sectional view showing the configuration of a detection cartridge 101 for a nucleic acid detector 10 according to variation 2 of the invention. FIG. 6 is a fragmentary cross-sectional view of the detection cartridge 101 as taken along line A-A in FIG. 2. With the detection cartridge 101 for the nucleic acid detector 10 according to variation 2 and as shown in this diagram, the probe-fixing area 1013 is provided not on the inside wall of each chamber 1011, but on the inside wall of the passage 1012. This configuration can also bring about an advantageous effect similar to that of the aforementioned embodiment of the invention.

While the invention has been described with respect to a limited number of embodiments, those skilled in the art, having benefit of this disclosure, will appreciate that other embodiments can be devised that do not depart from the scope of the invention as disclosed herein. Accordingly, the scope of the invention should be limited only by the attached claims.

What is claimed is:

1. A biogenic substance detection method comprising:
   a reaction step of supplying a sample solution to a plurality of chambers connected via a passage and having one of a plurality of biogenic substances contained in the sample solution react with one of a plurality of probes fixed in the chambers to detect the biogenic substance, a different probe being fixed in each of the chambers; and
   a detection step of detecting the biogenic substance that has reacted with the one probe;
   in the reaction step, the sample solution being made to move back and forth within the chambers and the passage along a chamber-passage alignment direction,
   the detection step comprising the steps of:
      moving a solution including a chemiluminescent enzyme back and forth within the chambers and the passage so that the chemiluminescent enzyme binds with the one of the biogenic substances that has reacted with the one of the probes;
      filling the chambers and the passage with a substrate liquid that reacts the chemiluminescent enzyme to produce a chemiluminescent substance; and
      resting the substrate liquid so as to produce the chemiluminescent substance, and
   the passage having a first cross-sectional area taken perpendicularly to the chamber-passage alignment direction that is smaller than a second cross-sectional area of each chamber taken perpendicularly to the chamber-passage alignment direction.

2. The biogenic substance detection method according to claim 1, wherein each probe is fixed to an entire inside wall surface of each chamber.

3. The biogenic substance detection method according to claim 1, wherein the chambers and the passage are made in a transparent plate, and
   wherein in the detection step, luminescence is measured through the chambers.

* * * * *